United States Patent [19]

Luber et al.

[11] Patent Number: 5,112,813

[45] Date of Patent: * May 12, 1992

[54] PROCESS FOR THE PREPARATION OF A VISCOSITY-STABLE ANTACID COMPOSITION

[75] Inventors: Joseph R. Luber, Lafayette Hills; Kenneth M. Feld, Chalfont; Richard J. Harwood, Bensalem; Wayne M. Grim, Doylestown, all of Pa.

[73] Assignee: Rhône-Poulenc Rorer Pharmaceuticals Inc., Fort Washington, Pa.

[*] Notice: The portion of the term of this patent subsequent to May 17, 2005 has been disclaimed.

[21] Appl. No.: 164,551

[22] Filed: Mar. 7, 1988

Related U.S. Application Data

[63] Continuation of Ser. No. 837,527, Mar. 7, 1986, Pat. No. 4,744,986.

[51] Int. Cl.$^5$ .................. A61K 31/715; A61K 31/10; A61K 33/08
[52] U.S. Cl. ..................... 514/54; 424/686; 424/690
[58] Field of Search ................... 424/686, 690; 514/54

[56] References Cited

U.S. PATENT DOCUMENTS 3,326,755 6/1987 Sheth .................................. 424/156
4,140,760 2/1979 Withington ........................ 424/125

Primary Examiner—Frederick E. Waddell
Assistant Examiner—Zohreh A. Fay
Attorney, Agent, or Firm—Martin E. Savitzky; James A. Nicholson; Alexis Barron

[57] ABSTRACT

A process for the preparation of a viscosity-stable antacid composition containing an alginic acid salt comprising reacting an antacid material with said salt at elevated temperatures to form a reaction product and recovering said reaction product in stabilized form.

11 Claims, No Drawings

PROCESS FOR THE PREPARATION OF A VISCOSITY-STABLE ANTACID COMPOSITION

This is a continuation of co-pending application Ser. No. 837,527 filed on Mar. 7, 1986 now U.S. Pat. No. 4,744,986.

FIELD OF THE INVENTION

The present invention relates to the preparation of pharmaceutical compositions which are useful for treating esophageal and gastrointestinal irritations.

Esophageal pain, commonly experienced as heartburn, is symptomatic of gastric reflux. Gastric reflux occurs when small amounts of gastric juice and/or bile acids pass into the lower part of the esophagus and cause esophageal irritation. Typically, gastric reflux, which occurs after meals, especially large meals, is aggravated by bending over or lying down, and is a common occurrence in patients having a hiatal hernia, or a weakening of the esophageal sphincter. Severe episodes of gastric reflux may inflame the esophageal mucosa and lead to the more serious condition of reflux esophagitis in which severe damage or loss of squamous epithelium of the lower part of the esophagus may occur. If esophagitis is persistent or severe, an inflammatory blockage of the esophagus may develop.

Persistent gastric reflux has been treated by attempting to reduce gastric volume, acidity of the gastric contents, and accelerate gastric emptying. Reduction in gastric acid is commonly effected by frequent ingestion, for example, in hourly intervals, of antacid preparations such as aluminum hydroxide gel or magnesium hydroxide, etc. Other methods of treating gastric reflux include the administration of drugs such as bethanechol (Urecholine) and metachlopramide (Reglan), which increase the tone of the lower esophageal sphincter and accelerate gastric emptying. If these methods do not reverse the inflammatory process, surgical therapy is often recommended.

Another approach to the problem of gastric reflux comprises the administration of a preparation which forms a gelatinous foam or raft which floats on the stomach contents. The foam-containing antacid precedes the stomach contents into the esophagus when reflux occurs and helps to protect the mucosa from further irritation. The gelatinous foam is formed by the combination of an acid insoluble gelatinous material entrapping $CO_2$ gas. The present invention relates to improvements in the formulation of preparations which are capable of forming such foams.

REPORTED DEVELOPMENTS

Heretofore known preparations used to create the aforementioned type foams comprise sodium bicarbonate and either solid compositions or liquid suspensions of alginic acid or its sodium salt. Exemplary of such prior art preparations include the product Gaviscon (Marion Laboratories) and compositions described in U.S. Pat. No. 4,140,760. Such known compositions contain relatively small amounts of antacid material and relatively large amounts of sodium. Accordingly, they are not particularly effective when used by patients who require a substantial adjustment of gastric pH and/or problems can be encountered when they are used by patients who should not receive an excessive amount of sodium.

In copending U.S. patent application Ser. No. 601,796, assigned to the same assignee as the present invention, an antacid composition which includes magnesium alginate and which is useful for the suppression of gastric reflux is disclosed. Preferred embodiments of such magnesium alginate-containing composition have a low sodium content and include relatively large amounts of aluminum-containing antacid materials. The '796 application further discloses that such compositions can be formulated in the convenient and palatable dosage form of an aqueous suspension. A problem encountered with such aqueous suspensions which comprise an antacid material and a salt of alginic acid is that they exhibit a tendency to fluctuate unpredictably in viscosity, to gel and to form lumps.

The present invention relates to a process for the preparation of a viscosity-stable antacid suspension useful for the treatment of reflux esophagitis.

SUMMARY OF THE INVENTION

In accordance with the present invention, there is provided a method for the preparation of a viscosity-stable aqueous antacid suspension containing an alginic acid salt comprising the following sequential steps:
(A) forming an aqueous mixture of an alginic acid salt and an antacid material;
(B) forming a reaction product under conditions which include heating said mixture to an elevated temperature; and
(C) recovering the reaction product in a stabilized form which is capable of being used as a viscosity stable aqueous antacid composition.

In preferred form the aqueous mixture is heated to a temperature within the range of about 60° C. to about 90° C. for a period of time sufficient to form the reaction product and said product is cooled to ambient temperature in a relatively short period of time, for example, within several minutes.

This invention encompasses also a viscosity-stable aqueous antacid suspension containing a salt of alginic acid. An advantage of such a suspension is that it is stable for a relatively long period of time, for example, for at least about one year.

Another advantage of the present invention flows from the nature of the antacid material used in the aqueous suspension of the composition. By way of background, it is noted that the amount of antacid material that could be effectively incorporated heretofore in known floating antacid compositions was relatively small, and accordingly, such compositions were capable of neutralizing a limited amount of acid and did not substantially change the gastric pH. The present invention makes it possible to include in the composition a relatively large amount of antacid material which is effective in neutralizing excess gastric acid present in the stomach.

Additional aspects of the present invention are discussed below.

DETAILED DESCRIPTION

The term "viscosity-stable" describes the ability of the present aqueous antacid compositions to maintain a relatively stable viscosity starting from the time of formulation and continuing for a period of weeks, months and/or years at room temperature or at the slightly higher temperatures of about 40° C. to about 50° C. A viscosity value is considered to be stable, if over a period of about twelve weeks, viscosity changes do not exceed about 50% at room temperature to 40° C. or about 130% at about 50° C.

The antacid material is any material which is pharmaceutically acceptable and which is capable of neutralizing aqueous acid and in particular gastric acid. The antacid material may be a silicate-, hydroxyl-, carbonate- or bicarbonate-containing material such as aluminum hydroxide, magnesium hydroxide, magnesium trisilicate, magnesium carbonate or bicarbonate, sodium carbonate or bicarbonate, potassium carbonate or bicarbonate, calcium carbonate or bicarbonate or complexes thereof. Complex antacids include the naturally occurring and synthetic materials such as hydrotalcite, magaldrate or complexes containing a nonstoichiometric mixture of carbonate, hydroxyl, sulfate, phosphate, silicate, aluminum and magnesium ions.

The preferred antacid material comprises magnesium carbonate and aluminum hydroxide as separate ingredients and/or in a combined form. This includes codried or coprecipitated powders of magnesium carbonate and aluminum hydroxide, and compounds such as the hydrotalcites having a formula $(Al)_w(Mg)_x(OH)_y(CO_3)_z$ and described in U.S. Pat. No. 4,351,814, hereby incorporated by reference. Preferred combined forms of material include $Al(OH)_3$ in an amount of about 30 to about 40% (as $Al_2O_3$) and $MgCO_3$ in an amount of about 5 to about 20% (as MgO). A preferred composition is sold by Societe Des Products Chemiques Alumineux (SPCA) and contains about 35% $Al_2O_3$ and about 12% MgO.

A particularly preferred antacid material for use in the practice of the present invention comprises an aluminum-containing ingredient including active and complexed aluminum and a magnesium carbonate ingredient in a ratio of about 1:1 to about 1:2. The term "active aluminum" means aluminum ions which have available reactive sites capable of reacting with a carboxylate anion such as an alginate anion. Active aluminum is present in aluminum compounds containing hydroxyl, carbonate or other weakly bonded ligands. The term "complexed aluminum" means aluminum which has no available active sites and which is not capable under room temperature and atmospheric pressure conditions of forming a reaction product with a carboxylate anion such as an alginate anion. Aluminum-magnesium complexes are examples of antacid materials containing complexed as well as active aluminum.

The total amount of antacid material present in the composition comprises an amount which when used in a method for the treatment of excess stomach acid is at least sufficient to neutralize excess gastric acid present in the stomach. The preferred aqueous suspensions of the present invention include an amount of antacid material which provides an acid-neutralizing capacity of about 1 to about 3 mEq/ml of suspension. The antacid material may be present in the composition of the present invention in an amount of about 20 to about 120 g/l.

Alginate salts for use in the practice of the present invention can be prepared, for example, from alginic acid, which is a polymeric material composed of 1,4' linked residues of α-D-mannuronic acid and β-L-guluronic acid. The proportions of mannuronic to guluronic acid residues varies and depends on the brown algae source from which the alginate is extracted. Table 1 shows the compositions of alginic acid obtained from various types of commercially important brown algae.

TABLE 1

Mannuronic Acid (M) and Guluronic Acid (G) Composition of Alginic Acid Obtained from Commercial Brown Algae

| Species | M Content (%) | G Content (%) | M/G Ratio | M/G Ratio Range |
|---|---|---|---|---|
| Macrocystis pyrifera | 61 | 39 | 1.56 | — |
| Ascophyllyum nodosum | 65 | 35 | 1.85 (1.1) | 1.40–1.95 |
| Laminaria digitata | 59 | 41 | 1.45 | 1.40–1.60 |
| Laminaria hyperborea (stipes) | 31 | 69 | 0.45 | 0.40–1.00 |
| Ecklonia cava and Eisenia bicyclis | 62 | 38 | 1.60 | — |

A thorough discussion of the structure and properties of alginic acid and a number of its commercially available salts is found in the trade publication of Kelco, Division of Merck and Co., Inc., entitled "Algin/hydrophilic Derivatives of Alginic Acid for Scientific Water Control" (second edition).

The varying composition of alginic acid and its derivatives is reflected in variations in certain of its physical properties including viscosity. Viscosity measurements of commercially available alginates using a Brookfield Model LVF Viscometer at 60 rpm with the appropriate spindle at 25° C. of 1 to 2% solutions range from about 10 cps to about 17,000 cps.

The amount of alginate salt present in the present composition is an amount which is sufficient to form a rigid or semi-rigid gel matrix throughout a substantial portion of an acidic medium. Preferably, the weight ratio of alginate salt to antacid material ranges from about 1:1 to about 1:2.

The preferred alginic acid salt for use in the present invention is the magnesium salt of alginic acid, although other salts may be used including, the sodium and potassium salts. The most preferred magnesium alginate exhibits a viscosity in a 7.5 wt. % solution, of about 10 to about 2000 cps, and preferably about 1000 to about 1700 cps, measured at 25° C. by the Brookfield Model LVT Viscometer at 12 rpm, using spindle No. 2.

The preferred magnesium alginate ingredient may be obtained commercially from Protan Scotia Marine, Inc., or be prepared by a number of methods, including the method disclosed in copending application Ser. No. 601,796.

Compositions which contain, as essential ingredients, an antacid material and alginate salt as described above, and which are prepared according to the present invention as described below, are capable of being used as an antacid composition. However, it is believed that the more widely used compositions will also include a material which produces a nontoxic gas when contacted with aqueous acid such as gastric acid. The gas-producing material may also function as an antacid material or it may be a gas-producing material which does not have antacid properties. The preferred gas-producing material is potassium bicarbonate, which, as mentioned above, has antacid properties.

Compositions which include a gas-producing material form a gas, after ingestion, as a result of reacting with gastric acid in the stomach. The gas is trapped in the alginic acid gel formed by the composition and is responsible for creating a gelatinous foamy mass of lower bulk density than the gastric contents. The gelatinous mass floats to the surface of the gastric contents and forms a physical barrier to gastric reflux, and precedes stomach contents into the esophagus.

The gas-producing material is present in an amount which provides sufficient volume of gas to cause the alginic acid gel to float to the surface of the gastric contents. For this purpose, preferred amounts of the gas-producing material are equal to about one-eighth to about one-third the weight of alginic acid salt. The rigidity, strength and thickness of the foamy mass formed by contact with gastric acid will depend upon the ratio of the gas-producing material to the alginate, upon the viscosity of the alginate, and on the presence of any divalent cations which function as a cross-linking agent. In certain applications of the present invention it is believed to be beneficial to include in the composition an effective cross-linking amount of a divalent cation such as calcium in the form of a salt, for example, calcium carbonate.

Compositions of the present invention in the form of suspensions should be stable for relatively long periods of time, for example, one to two years, or at least be capable of being reconstituted by agitation subsequent to separation. In suspensions, the settling of a "suspendant" in concentrated compositions can be a major problem. The foregoing problem can be inhibited or deterred by the use of a suspension stabilizer and, as noted above, the use of a combined form of magnesium carbonate and aluminum hydroxide. The suspension stabilizer is included in an amount which is effective to maintain the antacid material in suspension. The choice of stabilizer will depend on various factors, including the amount and viscosity grade of the alginate used in the composition and the amount, density and particle size of the antacid material. Preferably, the aqueous suspensions contain from 0.1 to 1.5% weight/volume of any pharmaceutically acceptable stabilizer which preferably does not contain sodium. Exemplary suspension stabilizers include tragacanth, guar gum, solka-floc, carrageenan, pectin, pregelatinized potato starch, citric acid, hydroxypropylmethylcellulose and Xanthan gum.

It is preferred that compositions within the scope of the present invention have a long shelf life and resist being deteriorated by microorganisms. Consequently, the compositions should contain a preservative. A combination of methyl and propyl p-hydroxybenzoates (methyl and propyl paraben) may be employed, for example, in an amount of about 0.25% and about 0.1% weight/volume, respectively. The suspension may include antioxidants to prevent discoloration over time and may also include one or more of coloring, sweetening or flavoring agents.

In preferred form, compositions prepared in accordance with the present invention are substantially sodium free, that is, the amount of sodium is no more than about 10 mg per 10 ml of an aqueous suspension of the composition.

A preferred aqueous suspension includes an effective amount of suspension stabilizer as described above and exhibits an acid-neutralizing capacity of about 1 to about 3 mEq/ml and a viscosity of about 100 to about 1000 centipoise.

A particularly preferred suspension prepared according to the present invention comprises about 30 to about 90 mg/ml of magnesium alginate, about 10 to about 50 mg/ml of magnesium carbonate, about 10 to about 50 mg/ml of a combined form of aluminum hydroxide and magnesium carbonate and about 2 to about 20 mg/ml of potassium bicarbonate.

Turning now to a description of the method of the present invention for preparing a viscosity-stable aqueous antacid suspension, the present method includes the step of forming a reaction product under conditions which include heating an aqueous mixture of an alginic acid salt and an antacid material.

It should be understood that certain antacid materials described above are capable of degrading, for example through the loss of $CO_2$, when subjected to heating in accordance with particular embodiments of the present process, but that the compositions of the present invention may nevertheless include such antacid materials if they are introduced into the composition subsequent to the heating step.

In the practice of this method, the aqueous mixture of the antacid material and the alginate salt is heated to an elevated temperature for a period of time sufficient to form a reaction product. For example, there can be employed a flash heating process, such as involving the use of pasteurization, of about 60° C. to about 90° C. for about 10 to about 80 sec, or a slower process involving the heating of the aqueous mixture to the elevated temperature of about 60° C. to about 90° C. for about 20 to about 40 minutes or a combination of both processes.

The reaction product can be recovered by reducing the temperature of the hot reaction product to ambient temperature. This can be accomplished, for example, by the natural loss of heat to the surrounding environment. However, in preferred form, the stabilized reaction product is recovered by utilizing means to extract heat therefrom at a faster rate than occurs through natural cooling. Temperature reduction may be effected, for example, by refrigeration which can be a part of a heating/cooling loop or by mixing the hot reaction product with a cooler aqueous composition. The temperature of the reaction product is reduced typically to a stabilization temperature of about 20° C. to about 45° C., preferably to about 30° C. to about 40° C.

The preferred method of reducing the temperature of the reaction product comprises the use of a temperature-lowering amount of aqueous composition, that is, a composition having a lower temperature than that of the reaction product and with which the reaction product is mixed. Thus, the reaction product can be cooled by pumping, pouring, injecting or spraying, it into the cooler aqueous composition. The heat present in the reaction product dissipates into the aqueous composition, which acts as a heat sink. Said cooler aqueous composition, prior to mixing with the reaction product, can have a temperature of about 0° C. to about 30° C., and preferably has a temperature of about 15° C. to about 25° C.

A preferred embodiment of this invention comprises the temperature-quenching of the hot reaction product, that is, the temperature of the heated reaction mixture is reduced quickly to a lower stabilization temperature in about 10 sec to about 2 minutes. One means of quenching the reaction mixture is by providing a sufficient volume of aqueous composition to effect a sufficiently rapid reduction of temperature of the hot reaction product. For this purpose, it is recommended that there be used the preferred volume ratio of reaction product to aqueous composition of about one to about three to twenty.

The preferred temperature-reducing aqueous composition is an aqueous carbonate-containing composition, most preferably an aqueous suspension of magnesium carbonate. The concentration of the aqueous carbonate-containing composition may range from about 5 to about 100 g/liter and preferably from about 60 to about 90 g/liter.

A preferred process according to the present invention comprises:

(D) use, as the antacid material in forming the reaction product, of an antacid material comprising complexed and active aluminum, and heating the aqueous reaction mixture until substantially all of said active aluminum has reacted with said alginate; and (E) cooling the resulting hot reaction product by combining it with an aqueous suspension of a carbonate-containing material of lower temperature.

When using an "active aluminum" antacid material, it is preferred that substantially all of it be included in the aqueous mixture of step (D) above.

Another preferred embodiment of the present invention comprises the steps of:

(F) forming an aqueous mixture of a co-precipitated aluminum hydroxide/magnesium carbonate gel comprising active and complexed aluminum and a first portion of magnesium alginate;

(G) heating said aqueous mixture to a reaction temperature for a period of time sufficient to react substantially all of said active aluminum with said first portion of magnesium alginate;

(H) cooling said heated mixture by combining it with an aqueous suspension of magnesium carbonate of lower temperature; and (I) combining the cooled reaction product with a second portion of magnesium alginate.

In a highly preferred embodiment of the present invention, there is used in the aqueous mixture of step (F) above a relatively small portion of the total amount of alginate included in the viscosity-stable antacid suspension. The preferred amount of alginate in the aqueous mixture is about 3 to about 15 wt. % and most preferably about 5 to about 10 wt. % of the total amount of alginate.

Consideration has been given to the reason why use of the method of the present invention results in the formation of a viscosity-stable aqueous suspension of antacid material and a material which is so markedly different from heretofore known suspensions of the type that tend to fluctuate unpredictably in viscosity. It is believed that suspensions of the latter type include therein reactive materials which undergo over an extended period of time under storage or shelf conditions reactions which result in the formation of products which directly or indirectly have an effect on the viscosity of the suspension. Heating of a mixture of alginic acid salt and antacid material in accordance with the present invention is believed to result in an exhaustion or a substantial exhaustion of reactive materials or in the formation of materials which have little or no tendency to react further. As a consequence, the product of reaction is believed to be free or substantially free of materials which tend to cause either directly or indirectly significant changes in the viscosity of the suspension.

The present invention is illustrated by the following examples.

EXAMPLE 1

A mixture of magnesium alginate (2.5 g) and a co-precipitated aluminum hydroxide/magnesium carbonate dry gel [(28 g, SPCA-35% $Al_2O_3$, 12% MgO] in purified water (USP) (about 75 ml) is stirred at about 70° C. to about 80° C. for about 30 minutes. The heated reaction mixture is quickly poured with stirring into about 400 ml of an aqueous suspension of magnesium carbonate (35 g) having a temperature of about 25° C. The temperature of the resulting mixture becomes about 35° C. within about 30 seconds after initial mix of the compositions. A second portion of magnesium alginate (47.5 g) is added to the stirred mixture. This is followed by the addition of the following additives in the amounts indicated below.

|  | g/liter |
|---|---|
| Xanthan Gum | 1 |
| Calcium Carbonate | 15 |
| Potassium Bicarbonate USP | 10 |
| Methyl Paraben USP | 2.5 |
| Propyl Paraben USP | 1 |
| Calcium Saccharin | 0.3 |
| Sorbitol USP | 20 |
| Flavors | — |

Purified water is added to reach a volume of about one liter and the final suspension is milled using a colloid mill. The resulting product has a smooth consistency, is flowable and is physically and chemically stable over a period of about six months at ambient temperature. The suspension has an acid neutralizing capacity of about 8.2 mEq/5ml (about 1.6 mEq/ml) and a sodium content of less than 4 mg per 5 ml.

Table 2 below presents the results of a comparative study of the viscosities of antacid suspensions prepared in accordance with the present invention and suspensions prepared simply by combining the identical starting materials into the final suspension. Viscosity measurements made over a period of 12 weeks are indicated below under the column designating the temperature at which the composition was maintained and the time at which the measurement was made after formulation. Blank spaces under a column represent that a viscosity measurement for a particular composition was not made at the particular time and temperature. The viscosity of compositions prepared according to the present invention are identified below as Examples 2 to 4. The viscosity of the comparative compositions are identified as Examples C-1 to C-9.

TABLE 2

| | | Viscosity (cps) | | | | | | | | |
|---|---|---|---|---|---|---|---|---|---|---|
| | | 4 weeks | | | 8 weeks | | | 12 weeks | | |
| Example | Initial | RT | 40° C. | 50° C. | RT | 40° C. | 50° C. | RT | 40° C. | 50° C. |
| 2 | 377 | 480 | 440 | 680 | 440 | 560 | 805 | 560 | 540 | 865 |
| 3 | 440 | 575 | 475 | 460 | 665 | 515 | 640 | 675 | 565 | 840 |
| 4 | 553 | 715 | 535 | 600 | 850 | 625 | 810 | 775 | 590 | 760 |
| C-1 | 325 | 490 | 430 | 1260 | 660 | 565 | 1325 | 690 | 900 | 1490 |
| C-2 | 319 | 450 | 510 | 1950 | 540 | 615 | 2080 | 605 | 1350 | 2240 |
| C-3 | 342.5 | 420 | 250 | 925 | 530 | 225 | 1080 | 625 | 425 | 1475 |
| C-4 | 681 | 1025 | 1575 | >2500 | | 1725 | >2500 | 1325 | 2290 | |
| C-5 | 696 | 1060 | 1125 | 1750 | 1030 | 1310 | 2010 | 1180 | 1995 | |

TABLE 2-continued

| | | Viscosity (cps) | | | | | | | | |
|---|---|---|---|---|---|---|---|---|---|---|
| | | 4 weeks | | | 8 weeks | | | 12 weeks | | |
| Example | Initial | RT | 40° C. | 50° C. | RT | 40° C. | 50° C. | RT | 40° C. | 50° C. |
| C-6 | 694 | 1160 | 1525 | 1925 | 1140 | 1705 | | 1350 | 1990 | |
| C-7 | 765 | 925 | 760 | >2500 | 1225 | 720 | >2500 | 1410 | 940 | >2500 |
| C-8 | 887 | 960 | 1425 | 1915 | 1410 | 1725 | >2500 | 1540 | 2375 | >2500 |
| C-9 | 451 | 590 | 900 | 1410 | 950 | 960 | 1970 | 1190 | 1410 | 1980 |

We claim:

1. A viscosity-stable aqueous antacid composition containing an alginic acid salt and a stabilized aluminum-containing antacid, and prepared by the process comprising:
   (A) forming an aqueous mixture of an alginic acid salt and an aluminum-containing antacid material having a tendency to form reaction products which effect the viscosity of said composition:
   (B) forming a stabilized reaction product comprising said stabilized aluminum-containing antacid under conditions which include heating said aqueous mixture to an elevated temperature; and
   (C) recovering the stabilized reaction product in a form which is capable of being used as a viscosity-stable aqueous antacid composition.

2. A viscosity-stable aqueous antacid composition consisting essentially of an effective acid-neutralizing amount of an antacid material comprising an aluminum-containing antacid not having a tendency to form reaction products which effect the viscosity of said composition, and an amount of magnesium alginate effective to attain a viscosity of about 400 to about 800 cps.

3. A composition according to claim 2 wherein the amount of said antacid material is about one to about two times the amount of said alginate in said composition and said aluminum-containing antacid comprises co-precipitated aluminum hydroxide/magnesium carbonate gel.

4. A composition according to claim 3 in the form of an aqueous suspension comprising about 10 to about 50 mg/ml of said aluminum-containing antacid, about 30 to about 90 mg/ml of magnesium alginate, about 10 to about 50 mg/ml of magnesium carbonate and about 2 to about 20 mg/ml of potassium bicarbonate.

5. A composition according to claim 2 in the form of an aqueous suspension which is substantially free of sodium.

6. A composition according to claim 1 in the form of an aqueous suspension wherein
   (D) said aqueous mixture is heated until substantially all of said aluminum having a tendency to form reaction products which effect the viscosity of said composition has reacted with said salt; and
   (E) cooling said product by combining it with an aqueous suspension of a carbonate-containing material of a lower temperature.

7. A composition according to claim 1 in the form of an aqueous suspension including
   (F) forming an aqueous mixture of a co-precipitated aluminum hydroxide/magnesium carbonate gel and a first portion of magnesium alginate;
   (G) heating said mixture to a reaction temperature for a period of time sufficient to react substantially all of said aluminum having a tendency to form reaction products which effect the viscosity of said composition with said first portion of magnesium alginate;
   (H) cooling said heated mixture by combining it with an aqueous suspension of magnesium carbonate of lower temperature; and
   (I) combining the cooled reaction product obtained in step (H) with a second portion of magnesium alginate.

8. An aqueous antacid suspension having viscosity-stable properties, capable of forming a floating gelatinous mass when contacted with aqueous acid, and comprising magnesium alginate, an antacid material including an aluminum-containing antacid which does not have a tendency to form reaction products which effect the viscosity of said composition, said antacid material being present in an effective acid-neutralizing amount that is about one to two times the weight amount of said magnesium alginate, and a non-toxic gas-producing material in an effective gas-volume-producing amount which is about one-third to about one-eighth the weight amount of said magnesium alginate.

9. A suspension according to claim 8 and having a viscosity which does not change more than about 50% over a period of about twelve weeks while maintained at a temperature between room temperature and about 40° C.

10. A suspension according to claim 9 wherein said antacid material comprises co-precipitated aluminum hydroxide/magnesium carbonate gel.

11. A suspension according to claim 9 comprising about 10 to about 50 mg/ml of said aluminum-containing antacid in a combined form of aluminum hydroxide and magnesium carbonate, about 30 to about 90 mg/ml of magnesium alginate, about 10 to about 50 mg/ml of magnesium carbonate and about 2 to about 20 mg/ml of potassium bicarbonate.

* * * * *